(12) United States Patent
Chen et al.

(10) Patent No.: US 10,647,742 B2
(45) Date of Patent: May 12, 2020

(54) METHOD FOR SYNTHESIZING ETELCALCETIDE

(71) Applicant: HYBIO PHARMACEUTICAL CO., LTD., Shenzhen, Guangdong (CN)

(72) Inventors: Yonghan Chen, Guangdong (CN); Pengcheng Mi, Guangdong (CN); Anjin Tao, Guangdong (CN); Jiancheng Yuan, Guangdong (CN)

(73) Assignee: HYBIO PHARMACEUTICAL CO., LTD., Shenzhen, Guangdong (CN)

(*) Notice: Subject to any disclaimer, the term of this patent is extended or adjusted under 35 U.S.C. 154(b) by 12 days.

(21) Appl. No.: 16/067,450

(22) PCT Filed: Dec. 20, 2016

(86) PCT No.: PCT/CN2016/111098
§ 371 (c)(1),
(2) Date: Jun. 29, 2018

(87) PCT Pub. No.: WO2017/114240
PCT Pub. Date: Jul. 6, 2017

(65) Prior Publication Data
US 2019/0010185 A1  Jan. 10, 2019

(30) Foreign Application Priority Data

Dec. 31, 2015 (CN) .......................... 2015 1 1029990

(51) Int. Cl.
| | | |
|---|---|---|
| *A61K 38/08* | (2019.01) | |
| *C07K 1/00* | (2006.01) | |
| *C07K 7/06* | (2006.01) | |
| *C07K 7/02* | (2006.01) | |
| *C07K 1/04* | (2006.01) | |
| *C07K 1/06* | (2006.01) | |

(52) U.S. Cl.
CPC .............. *C07K 1/003* (2013.01); *A61K 38/08* (2013.01); *C07K 1/006* (2013.01); *C07K 1/04* (2013.01); *C07K 7/02* (2013.01); *C07K 7/06* (2013.01); *C07K 1/061* (2013.01); *Y02P 20/55* (2015.11)

(58) Field of Classification Search
None
See application file for complete search history.

(56) References Cited

U.S. PATENT DOCUMENTS

| | | |
|---|---|---|
| 2011/0028394 A1 | 2/2011 | Karim et al. |
| 2014/0271915 A1 | 9/2014 | Perello |
| 2014/0315809 A1 | 10/2014 | Walter |

FOREIGN PATENT DOCUMENTS

| | | |
|---|---|---|
| CN | 102711789 A | 10/2012 |
| CN | 102875655 A | 1/2013 |
| CN | 102875665 A | 1/2013 |
| CN | 103012563 A | 4/2013 |
| CN | 103497245 A | 1/2014 |
| CN | 105504012 A | 4/2016 |
| WO | 2013071262 A1 | 5/2013 |
| WO | 2014210489 A1 | 12/2014 |
| WO | 2015154031 A1 | 10/2015 |
| WO | WO-2015154031 A1 * | 10/2015 |

OTHER PUBLICATIONS

Protein Technologies, Inc., "Introduction to Fmoc Solid Phase Peptide Synthesis", 2006; pp. 1-6 (Year: 2006).*
ChemPep Inc., "Fmoc Solid Phase Peptide Synthesis", pp. 1-11, 2007 (Year: 2007).*
Merck Millipore, Novabiochem—Guide to selection of building blocks, 2012, pp. 1-18 (Year: 2012).*
Barlos et al., "Synthesis of the very acid-sensitive Fmoc-Cys(Mmt)-OH and its application in solid-phase peptide synthesis", Int. J. Peptide Protein Res., 1996, 148-153 (Year: 1996).*
The European search report dated Jul. 12, 2019 for European Application No. EP16881029.9.
International Search Report for PCT/CN2016/111098 dated Mar. 30, 2017, ISA/CN.

* cited by examiner

*Primary Examiner* — Lianko G Garyu
(74) *Attorney, Agent, or Firm* — Yue (Robert) Xu; Apex Attorneys at Law, LLP

(57) ABSTRACT

Provided is a method for solid phase synthesis of Etelcalcetide, comprising synthesizing Etelcalcetide backbone peptide resin, removing the side chain protecting group of Cys in the peptide chain, and then activating the sulfydryl group of the Cys side chain on the peptide resin with 2,2'-dithiodipyridine and constructing a disulfide bond with L-Cys, such that a crude Etelcalcetide peptide is obtained by cleaving. The method does not require undergoing multi-step purification, the yield and purity of the obtained crude peptide are relatively high, and the total yield of the refined peptide after purification is greatly increased.

10 Claims, No Drawings
Specification includes a Sequence Listing.

METHOD FOR SYNTHESIZING ETELCALCETIDE

This application is a US National Phase application based upon PCT Application No. PCT/CN2016/111098, filed Dec. 20, 2016, which claims priority to Chinese Patent Application No. 201511029990.2, entitled "METHOD FOR SYNTHESIZING ETELCALCETIDE", filed on Dec. 31, 2015 with the State Intellectual Property Office of People's Republic of China, the disclosures of which are incorporated herein by reference in its entirety.

INCORPORATION-BY-REFERENCE OF SEQUENCE LISTING

A computer-readable sequence listing is concurrently submitted as a text file and is hereby incorporated by reference in its entirety. The text file is 423 bytes, was created on Jun. 27, 2018, and is named 180073-FSU-HYBIO-Sequence-Listing.txt.

FIELD

The present invention relates to the field of medicine synthesis, specifically to a method for synthesizing Etelcalcetide.

BACKGROUND

Secondary hyperparathyroidism (SHPT, secondary hyperparathyroidism) refers to a chronic compensatory clinical manifestation in which parathyroid glands are stimulated by hypocalcemia, hypomagnesemia, or hyperphosphatemia for a long-term to secrete excessive parathyroid hormone (PTH) to increase blood calcium, blood magnesium and reduce blood phosphorus in the case of chronic renal insufficiency, intestinal malabsorption syndrome, Fanconi syndrome and renal tubular acidosis, vitamin D deficiency or resistance, as well as pregnancy, lactation, etc. Long-term parathyroid hyperplasia eventually leads to the formation of functionally autonomous adenomas.

Etelcalcetide is a novel calcimimetic agent developed by Kai Pharmaceuticals, Inc., which can inhibit the secretion of parathyroid hormone (PTH). Secondary hyperparathyroidism (SHPT) is a common and severe decompensation disorder in patients with chronic kidney disease (CKD) undergoing dialysis treatment. It is currently known that persistently elevated parathyroid hormone (PTH) is associated with a key clinical outcome in patients with CKD. Etelcalcetide can bind to and activate calcium-sensing receptors on the parathyroid glands to reduce parathyroid hormone (PTH) levels.

Etelcalcetide consists of three D-configuration arginines, two D-configuration alanines, one D-configuration argininamide, one D-configuration cysteine, and one L-configuration cysteine (the N-terminus is blocked by acetyl), wherein the D-configuration cysteine and the L-configuration cysteine are linked together by a disulfide bond (N-acetyl-D-cysteinyl-D-alanyl-D-arginyl-D-arginyl-D-arginyl-D-alanyl-D-Argininamide, disulfide with L-cysteine), the structure of which is shown below:

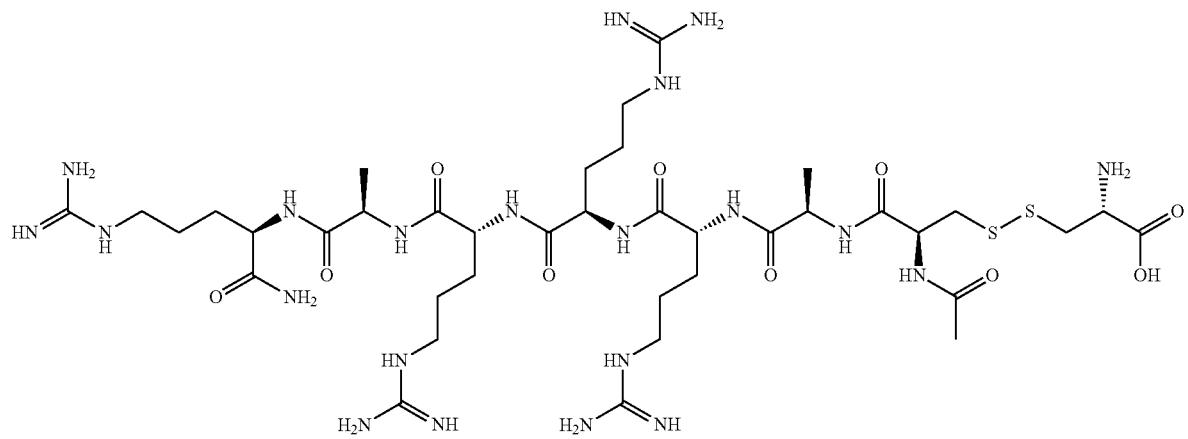 [SMILES: CC(=O)N[C@H](CSSC[C@H](N)C(=O)O)C(=O)N[C@H](C)C(=O)N[C@H](CCCNC(=N)N)C(=O)N[C@H](CCCNC(=N)N)C(=O)N[C@H](CCCNC(=N)N)C(=O)N[C@H](C)C(=O)N[C@H](CCCNC(=N)N)C(N)=O]

Patent CN201080045024.9 first reported this compound, but no synthesis process of the compound was reported. The key to the synthesis of this compound lies in the construction of intermolecular disulfide bonds. The conventional intermolecular disulfide bond construction generally requires the purification and preparation of two peptide fragments, followed by activation of one of the sulfydryl groups, then reaction with another sulfydryl group to form a disulfide bond after purification and preparation, and finally purification of the corresponding products obtained after the preparation. However, the reaction steps of the method are relatively tedious, requiring multi-step purification for preparation, the production cost is correspondingly high, and the final total yield is low.

SUMMARY

In view of this, the object of the present invention is to provide a method for synthesizing Etelcalcetide, such that the method can obtain crude peptide products with higher purity and yield without multi-step purification, and at the same time increase the total yield of the refined peptide.

To achieve the above object, the present invention provides the following technical solutions.

A method for synthesizing Etelcalcetide, comprising the steps of:

step 1: synthesizing by solid-phase synthesis a peptide resin of fragment A, in which protecting groups are coupled to side chains of D-Cys and D-Arg in the amino acid sequence shown in SEQ ID NO: 1, an amino resin is coupled to C-terminus of the amino acid sequence shown in SEQ ID NO: 1 and N-terminus is acetylated;

step 2: removing the protecting group from the side chain of D-Cys in the peptide resin of fragment A to obtain a peptide resin of fragment B;

step 3: activating the sulfhydryl group of the side chain of D-Cys in the peptide resin of fragment B with 2,2'-dithiodipyridine to obtain a peptide resin of fragment C; and step 4: coupling L-Cys coupled with a protecting group at the N-terminus thereof to the peptide resin of fragment C in a coupling system to construct a disulfide bond, obtaining a fully protected peptide resin, and adding a cleaving solution to remove all protecting groups and amino resin to obtain a crude peptide of Etelcalcetide.

In the present invention, a fully protected Etelcalcetide backbone peptide resin is synthesized all by solid-phase synthesis, and the protecting group of the Cys side chain in the peptide resin is removed, the sulfhydryl group on the D-Cys side chain in the peptide resin is activated with 2,2'-dithiodipyridine (substituting hydrogen with sulfhydrylpyridyl), a coupling reaction is performed by adding L-Cys coupled to a protecting group at the N-terminus thereof to form an intermolecular disulfide bond in a solid-phase manner, thus avoiding multiple purification preparation steps, and the purity and yield of the obtained crude peptide product are also high. The Etelcalcetide backbone heptapeptide (the amino acid sequence shown in SEQ ID NO: 1 of the present invention) is numbered by the amino acid sequence from the N-terminus to the C-terminus, as shown in the following formula:

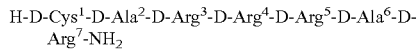

In the amino acid sequence shown in SEQ ID NO: 1, Xaa represents a D-amino acid, wherein Xaa(1)=D-Cys; Xaa(2, 6)=D-Ala; Xaa(3,4,5)=D-Arg, the number in parentheses indicates the amino acid number in the amino acid sequence shown in SEQ ID NO:1.

Wherein, preferably, the step 1 comprises:
coupling the protected D-Arg to the amino resin in the coupling system to obtain a protected D-Arg-amino resin, and according to the amino acid sequence shown in SEQ ID NO: 1 in the order from C-terminus to N-terminus, coupling protected D-Ala, protected D-Arg, protected D-Cys with N-terminal acetylation to the protected D-Arg-amino resin to obtain the peptide resin of fragment A.

Further preferably, the step 1 comprises:
step 1.1: coupling a Fmoc-D-Arg(Pbf)-OH to the amino resin in the coupling system to obtain a Fmoc-D-Arg(Pbf)-amino resin;

step 1.2: removing protecting group Fmoc to obtain H-D-Arg(Pbf)-amino resin, and coupling Fmoc-D-Ala-OH to the H-D-Arg(Pbf)-amino resin in the coupling system to obtain a Fmoc-D-Ala-D-Arg(Pbf)-amino resin;

step 1.3: according to the amino acid sequence shown in SEQ ID NO: 1 in the order from C-terminus to N-terminus, coupling one by one in sequence three Fmoc-D-Arg(Pbf)-OH, Fmoc-D-Ala-OH and N-Ac-D-Cys(Mmt)-OH according to the coupling manner of step 1.2 for amino acid extension to obtain a N-Ac-D-Cys(Mmt)-D-Ala-D-Arg(Pbf)-D-Arg(Pbf)-D-Arg(Pbf)-D-Ala-D-Arg(Pbf)-amino resin, that is, the peptide resin of fragment A; and wherein the Fmoc is N-terminal protecting group of amino acid, and the Pdf and Mmt are the protecting groups of amino acid side chain.

Preferably, the step 2 comprises:
removing the protecting group from the D-Cys side chain in the peptide resin of fragment A by adding a solution of TFA in DCM to the peptide resin of fragment A to obtain the peptide resin of fragment B.

Preferably, the coupling system involved in the method of the present invention is HOBt/DIC coupling system with two reagents or HBTU/HOBt/DIPEA coupling system with three reagents. Wherein, the molar ratio of each coupling reagent in the HOBt/DIC coupling system is preferably HOBt/DIC=1:(1~3); the molar ratio of each coupling reagent in the HBTU/HOBt/DIPEA coupling system with three reagents is preferably HBTU:HOBt:DIPEA=1:(1~3):(1~5), and the molar ratio of each protected amino acid to the coupling reagent is preferably 1:(1~5).

Preferably, the cleaving solution is an aqueous solution of TFA; more preferably, the volume percentage of TFA in the cleaving solution is 90~99%, and the balance is water.

Preferably, the L-Cys coupled with a protecting group at the N-terminus is preferably Boc-L-Cys-OH.

In the technical solutions of the present invention, the amino resin is a Rink amide resin, Rink amide AM Resin or Rink amide MBHA Resin, with a substitution degree of 0.2-1.0 mmol/g.

The protecting group described in the present invention is a protecting group used in the field of amino acid synthesis to protect groups that interfere with synthesis on the backbone and the side chain of the amino acids such as amino group, carboxyl group, sulfydryl group, and the like, and prevents an amino group, a carboxyl group, etc. from reacting during the preparation of a target product to generate impurities, while an amino acid protected by a protecting group is referred to a protected amino acid. In this technical field, groups that need to be protected on the amino acid side chains, the structure of the side chain, and how to couple the protecting groups are well known to those skilled in the art. The form of expression of an amino acid coupled to a protecting group in the present invention is also the form of expression commonly used in the art and is well known to those skilled in the art, for example, Fmoc-D-Arg(Pbf)-OH, wherein the Fmoc is a N-terminal protecting group of the amino acid, and the Pbf in parentheses is a protecting group of the Arg side chain. Unless specifically stated, other protected amino acid synthetic raw materials of the present invention can be explained with reference to this. It is specifically illustrated that, for Boc-L-Cys-OH protected amino acid, Boc is a N-terminal protecting group thereof.

The present invention preferably synthesizes a polypeptide fragment of interest by coupling one by one in solid-phase synthesis, and coupling one by one refers to that starting with the first amino acid, the remaining amino acids are subjected to a condensation reaction (the condensation reaction of amino and carboxyl group in the backbone) with the previous coupled amino acid one by one for coupling according to the sequence of the amino acid sequence shown in SEQ ID NO:1. In the coupling, since each amino acid has a protecting group at the N-terminus, it is necessary to remove the N-terminal Fmoc protecting group before coupling, which is the common general knowledge for those skilled in the art, and the present invention preferably uses DBLK (i.e., 20% piperidine in DMF, volume ratio) to remove the N-terminal protecting group. Due to the continuous coupling of amino acids, the synthesized polypeptide fragment is constantly changing, and preferably, the molar ratio of each protected amino acid raw material to be coupled to the previously synthesized peptide resin fragment is (2~10):1.

In addition, the amidation of the C-terminus of Etelcalcetide backbone heptapeptide in the present invention is achieved by coupling an arginine to an amino resin, and retaining the amino group on the amino resin after finally cleaving and removing all the protecting groups and the resin; moreover, the acetylation at the N-terminus can be achieved by acetylation of the N-terminus of cysteine so that it is subjected to liquid phase synthesis as the N-terminus, and the synthesis can also be carried out using commercially available acetylated cysteine.

The present invention can also perform RP-HPLC purification after obtaining Etelcalcetide crude peptide, and the RP-HPLC purification specifically comprises:

purifying the obtained Etelcalcetide crude peptide using NOVASEP RP-HPLC system with a wavelength of 220 nm, a chromatographic column of reversed-phase C18 column, a conventional 0.1% TFA/acetonitrile as mobile phase, desalting, collecting target peak fractions, concentrating by rotary evaporation, and lyophilizing to obtain a white refined peptide.

The Etelcalcetide crude peptide synthesized by the method of the present invention does not require multiple purifications, and the obtained purity is 80%~90%, and the yield is above 95%; meanwhile, by detecting after purification with RP-HPLC, the purity of the refined peptide is greater than 98%, and the total yield is 45~60%.

As can be seen from the above technical solutions, a solid-phase synthesis strategy is used in the present invention, in which Etelcalcetide backbone peptide resin is first synthesized, the side chain protecting group of D-Cys in the peptide chain is removed, and then the sulfydryl group of the D-Cys side chain on the peptide resin is activated with 2,2'-dithiodipyridine and a disulfide bond with L-Cys is constructed, and a Etelcalcetide crude peptide is obtained by cleaving. The whole process does not require multiple purifications, the yield and purity of the obtained crude peptide are relatively high, and the total yield of the refined peptide after purification is greatly increased.

DETAILED DESCRIPTION OF EMBODIMENTS

The present invention discloses a method for synthesizing Etelcalcetid, which can be achieved by those skilled in the art by properly improving process parameters in light of the disclosure. In particular, it should be noted that all similar substitutions and modifications will be apparent to those skilled in the art, and they are all considered to be included in the present invention. The method of the present invention has been described by the preferred examples, and it is apparent that related persons can make modifications or proper changes and combination to the compounds and preparation methods described herein so as to achieve and apply the technology of the present application, without departing from the content, spirit and scope of the present invention.

In the specific embodiments of the present invention, all the amino acids coupled to a protecting group are commercially available, the protected amino acid in the present invention is purchased from Gill Biochemical Co., Ltd., and the resin used is purchased from Tianjin Nankai Hecheng Co., Ltd. The meanings of the English abbreviations used in the application document are shown in Table 1.

TABLE 1

Meanings of English abbreviations

| Abbreviations (English) | Meaning |
| --- | --- |
| Fmoc | 9-fluorenylmethyloxycarbonyl |
| HOBt | 1-Hydroxybenzotriazole |
| DMF | N,N-Dimethylformamide |
| DCM | Dichloromethane |
| TFA | Trifluoroacetic acid |
| DIPEA | N,N-diisopropylethylamine |
| HOBT | 1-Hydroxybenzotriazole |
| HBTU | O-benzotrizaole-tetramethylurea hexafluorophosphate |
| Boc | Tert-butyloxycarbonyl |
| Etelcalcetide | A novel polypeptide drug developed by Kai Pharmaceuticals, Inc. |
| —OtBu | Tert-butyl ester |
| Fmoc | Fluorenylmethoxycarbonyl |
| Pbf | 2,2,4,6,7-pentamethyldihydrobenzofuran-5-sulfonyl chloride |

In the following, the present invention will be further elaborated in combination with Examples.

Example 1: Synthesis of N-Ac-D-Cys(Mmt)-D-Ala-D-Arg(Pbf)-D-Arg(Pbf)-D-Arg(Pbf)-D-Ala-D-Arg(Pbf)-Rink-Amide Resin 25.00 g of Rink-Amide resin with a substitution degree of 0.20 mmol/g was weighed and added to a solid-phase reaction column. The resin was washed twice with DMF, followed by swelling in DMF for 30 minutes. 20% piperidine/DMF (V/V) solution was added for 5+10 minutes to remove Fmoc. After the removal was completed, the resin was washed 6 times with DMF. The resin was detected by ninhydrin and showed color. 16.30 g (25 mmol) of Fmoc-D-Arg(Pbf)-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin (if the resin was colorless and transparent, the reaction was terminated; if the resin was colored, the reaction was prolonged for 1 hour, the same below).

At the end of the reaction, the resin was washed 3 times with DMF. 20% piperidine/DMF (V/V) solution was added for 5+10 minutes to remove Fmoc. After the removal was completed, the resin was washed 6 times with DMF. The resin was detected by ninhydrin and showed color. 7.80 g (25 mmol) of Fmoc-D-Ala-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin.

The subsequent amino acids were coupled successively by the same method. After the coupling was completed, the resin was shrunk and drained to give 35.50 g of the peptide resin of fragment A:

N-Ac-D-Cys(Mmt)-D-Ala-D-Arg(Pbf)-D-Arg(Pbf)-D-Arg(Pbf)-D-Ala-D-Arg(Pbf)-Rink-Amide Resin, and the weight gain rate of the resin was 97.5%.

Example 2: Synthesis of N-Ac-D-Cys(Mmt)-D-Ala-D-Arg(Pbf)-D-Arg(Pbf)-D-Arg(Pbf)-D-Ala-D-Arg(Pbf)-Rink-Amide Resin 11.10 g of Rink-Amide resin with a substitution degree of 0.45 mmol/g was weighed and added to a solid-phase reaction column. The resin was washed twice with DMF, followed by swelling in DMF for 30 minutes. 20% piperidine/DMF (V/V) solution was added for 5+10 minutes to remove Fmoc. After the removal was completed, the resin was washed 6 times with DMF. The resin was detected by ninhydrin and showed color. 16.30 g (25 mmol) of Fmoc-D-Arg(Pbf)-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin.

At the end of the reaction, the resin was washed 3 times with DMF. 20% piperidine/DMF (V/V) solution was added for 5+10 minutes to remove Fmoc. After the removal was completed, the resin was washed 6 times with DMF. The resin was detected by ninhydrin and showed color. 7.80 g (25 mmol) of Fmoc-D-Ala-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin.

The subsequent amino acids were coupled successively by the same method. After the coupling was completed, the resin was shrunk and drained to give 21.40 g of the peptide resin of fragment A, and the weight gain rate of the resin was 95.7%.

Example 3: Synthesis of N-Ac-D-Cys(Mmt)-D-Ala-D-Arg(Pbf)-D-Arg(Pbf)-D-Arg(Pbf)-D-Ala-D-Arg(Pbf)-Rink-Amide Resin 8.33 g of Rink-Amide resin with a substitution degree of 0.60 mmol/g was weighed and added to a solid-phase reaction column. The resin was washed twice with DMF, followed by swelling in DMF for 30 minutes. 20% piperidine/DMF (V/V) solution was added for 5+10 minutes to remove Fmoc. After the removal was completed, the resin was washed 6 times with DMF. The resin was detected by ninhydrin and showed color. 16.30 g (25 mmol) of Fmoc-D-Arg(Pbf)-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin.

At the end of the reaction, the resin was washed 3 times with DMF. 20% piperidine/DMF (V/V) solution was added for 5+10 minutes to remove Fmoc. After the removal was completed, the resin was washed 6 times with DMF. The resin was detected by ninhydrin and showed color. 7.80 g (25 mmol) of Fmoc-D-Ala-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin.

The subsequent amino acids were coupled successively by the same method. After the coupling was completed, the resin was shrunk and drained to give 18.40 g of the peptide resin of fragment A, and the weight gain rate of the resin was 94.3%.

Example 4: Removal of Mmt Protecting Group 10 g of the peptide resin of fragment A obtained in Example 1 was added to the reaction column, DMF was added to swell the resin for 30 min, and then DMF was removed. DMF was added to wash twice, and then DCM was added to wash twice. 100 ml of 2% TFA/DCM solution was added to react for 2 min and then removed, another 100 ml of 1% TFA/DCM solution was added to react for 2 min. This operation was repeated 15 times. The resin was washed 3 times with 100 ml of DCM and then washed 3 times with DMF. The resin was shrunk and drained to give 9.85 g of the peptide resin of fragment B: N-Ac-D-Cys-D-Ala-D-Arg(Pbf)-D-Arg(Pbf)-D-Arg(Pbf)-D-Ala-D-Arg(Pbf)-Rink-Amide Resin.

Example 5: Removal of Mmt Protecting Group 10 g of the peptide resin of fragment A obtained in Example 2 was added to the reaction column, DMF was added to swell the resin for 30 min, and then DMF was removed. DMF was added to wash twice, and then DCM was added to wash twice. 100 ml of 2% TFA/DCM solution was added to react for 2 min and then removed, another 100 ml of 2% TFA/DCM solution was added to react for 2 min. This operation was repeated 15 times. The resin was washed 3 times with 100 ml of DCM and then washed 3 times with DMF. The resin was shrunk and drained to give 9.80 g of the peptide resin of fragment B: N-Ac-D-Cys-D-Ala-D-Arg(Pbf)-D-Arg(Pbf)-D-Arg(Pbf)-D-Ala-D-Arg(Pbf)-Rink-Amide Resin.

Example 6: Removal of Mmt Protecting Group 10 g of the peptide resin of fragment A obtained in Example 3 was added to the reaction column, DMF was added to swell the resin for 30 min, and then DMF was removed. DMF was added to wash twice, and then DCM was added to wash twice. 100 ml of 3% TFA/DCM solution was added to react for 2 min and then removed, another 100 ml of 2% TFA/DCM solution was added to react for 2 min. This operation was repeated 15 times. The resin was washed 3 times with 100 ml of DCM and then washed 3 times with DMF. The resin was shrunk and drained to give 9.82 g of the peptide resin of fragment B: N-Ac-D-Cys-D-Ala-D-Arg(Pbf)-D-Arg(Pbf)-D-Arg(Pbf)-D-Ala-D-Arg(Pbf)-Rink-Amide Resin.

Example 7: Activation of Peptide Resin of Fragment B 7.7 g of 2,2'-dithiodipyridine was weighed and dissolved in 100 ml of DMF. 9.85 g of the peptide resin of fragment B of Example 4 was slowly added to the reaction solution and stirred to react for 2 hours. The reaction solution was drained, and the resin was washed 6 times with DMF. The resin was shrunk and drained to give 9.70 g of the peptide resin of fragment C in which the sulfydryl group of the Cys side chain was activated: N-Ac-D-Cys(SPyridine)-D-Ala-D-Arg(Pbf)-D-Arg(Pbf)-D-Arg(Pbf)-D-Ala-D-Arg(Pbf)-Rink-Amide Resin.

Example 8: Activation of Peptide Resin of Fragment B 15.4 g of 2,2'-dithiodipyridine was weighed and dissolved in 100 ml of DMF. 9.80 g of the peptide resin B of Example 5 was slowly added to the reaction solution and stirred to react for 2 hours. The reaction solution was drained, and the resin was washed 6 times with DMF. The resin was shrunk and drained to give 9.60 g of the peptide resin of fragment C in which the sulfydryl group of the Cys side chain was activated: N-Ac-D-Cys(SPyridine)-D-Ala-D-Arg(Pbf)-D-Arg(Pbf)-D-Arg(Pbf)-D-Ala-D-Arg(Pbf)-Rink-Amide Resin.

Example 9: Activation of Peptide Resin of Fragment B 30.8 g of 2,2'-dithiodipyridine was weighed and dissolved in 100 ml of DMF. 9.82 g of the peptide resin B of Example 6 was slowly added to the reaction solution and stirred to react for 2 hours. The reaction solution was drained, and the resin was washed 6 times with DMF. The resin was shrunk and drained to give 9.95 g of the peptide resin of fragment C in which the sulfydryl group of the Cys side chain was activated: N-Ac-D-Cys(SPyridine)-D-Ala-D-Arg(Pbf)-D-Arg(Pbf)-D-Arg(Pbf)-D-Ala-D-Arg(Pbf)-Rink-Amide Resin.

Example 10: Coupling of Boc-L-Cys-OH 9.70 g of the peptide resin of fragment C obtained in Example 7, in which the sulfydryl group of the Cys side chain has been activated, was added to a solid-phase reaction column, and DMF was added to swell the resin for 30 minutes. 3.12 g of Boc-L-Cys-OH and 1.0 ml of DIPEA were added to react at room temperature for 3 hours. After the coupling was completed, the reaction solution was drained and the resin was washed 6 times with DMF. The resin was shrunk and drained to give 10.21 g of the fully protected peptide resin.

Example 11: Coupling of Boc-L-Cys-OH 9.60 g of the peptide resin of fragment C obtained in Example 8, in which the sulfydryl group of the Cys side chain has been activated, was added to a solid-phase reaction column, and DMF was added to swell the resin for 30 minutes. 6.24 g of Boc-L-Cys-OH and 1.0 ml of DIPEA were added to react at room temperature for 3 hours. After the coupling was completed, the reaction solution was drained and the resin was washed 6 times with DMF. The resin was shrunk and drained to give 11.12 g of the fully protected peptide resin.

Example 12: Coupling of Boc-L-Cys-OH 9.95 g of the peptide resin of fragment C obtained in Example 9, in which the sulfydryl group of the Cys side chain has been activated, was added to a solid-phase reaction column, and DMF was added to swell the resin for 30 minutes. 9.36 g of Boc-L-Cys-OH and 1.0 ml of DIPEA were added to react at room temperature for 3 hours. After the coupling was completed, the reaction solution was drained and the resin was washed 6 times with DMF. The resin was shrunk and drained to give 12.20 g of the fully protected peptide resin.

Example 13: Cleaving of the Crude Product 10.21 g of the peptide resin obtained in Example 10 was added to a round-bottom flask, shaken at room temperature for 2 hours with 102 ml of trifluoroacetic acid:$H_2O$ (90:10), and filtered. The solution after cleaving was added to anhydrous diethyl ether to give 1.42 g of a yellow solid. The purity of the crude peptide was 81.5%, and the yield of the crude peptide was 96.20%.

Example 14: Cleaving of the Crude Product 11.12 g of the peptide resin obtained in Example 11 was added to a round-bottom flask, shaken at room temperature for 2 hours with 112 ml of trifluoroacetic acid:$H_2O$ (95:5), and filtered. The solution after cleaving was added to anhydrous diethyl ether to give 2.40 g of a yellow solid. The purity of the crude peptide was 80.8%, and the yield of the crude peptide was 98.01%.

Example 15: Cleaving of the Crude Product 11.80 g of the peptide resin obtained in Example 12 was added to a round-bottom flask, shaken at room temperature for 2 hours with 122 ml of trifluoroacetic acid:$H_2O$ (97.5:2.5), and filtered. The solution after cleaving was added to anhydrous diethyl ether to give 2.71 g of a yellow solid. The purity of the crude peptide was 81.0%, and the yield of the crude peptide was 95.16%.

Example 16: Purification of the Crude Peptide 1.42 g of the Etelcalcetide crude peptide prepared in Example 13 was subjected to purification using NOVASEP RP-HPLC system with a wavelength of 220 nm, a chromatographic column of reversed-phase C18 column, a conventional 0.1% TFA/acetonitrile as mobile phase, and desalted. Target peak fractions were collected, concentrated by rotary evaporation, and lyophilized to obtain 0.85 g of a white solid refined peptide with a purification yield of 59.86% and a mass spectrometry signal of 1048.5. The purity detected by HPLC was 98.50%, and the total yield was 57.81%.

Example 17: Purification of the Crude Peptide 1.50 g of the Etelcalcetide crude peptide prepared in Example 14 was subjected to purification using NOVASEP RP-HPLC system with a wavelength of 220 nm, a chromatographic column of reversed-phase C18 column, a conventional 0.1% TFA/acetonitrile as mobile phase, and desalted. Target peak fractions were collected, concentrated by rotary evaporation, and lyophilized to obtain 0.78 g of a white solid refined peptide with a yield of 53.06% and a mass spectrometry signal of 1048.4. The purity detected by HPLC was 98.50%, and the total yield was 52.0%.

Example 18: Purification of the Crude Peptide 1.50 g of the Etelcalcetide crude peptide prepared in Example 15 was subjected to purification using NOVASEP RP-HPLC system with a wavelength of 220 nm, a chromatographic column of reversed-phase C18 column, a conventional 0.1% TFA/acetonitrile as mobile phase, and desalted. Target peak fractions were collected, concentrated by rotary evaporation, and lyophilized to obtain 0.80 g of a white solid refined peptide with a yield of 53.33% and a mass spectrometry signal of 1048.5. The purity detected by HPLC purity was 98.50%, and the total yield was 49.48%.

Example 19: Synthesis of Etelcalcetide by Conventional Methods

1. Synthesis of N-Ac-D-Cys(Trt)-D-Ala-D-Arg(Pbf)-D-Arg(Pbf)-D-Arg(Pbf)-D-Ala-D-Arg(Pbf)-Rink-Amide Resin 25.00 g of Rink-Amide resin with a substitution degree of 0.20 mmol/g was weighed and added to a solid-phase reaction column. The resin was washed twice with DMF, followed by swelling in DMF for 30 minutes. 20% piperidine/DMF (V/V) solution was added for 5+10 minutes to remove Fmoc. After the removal was completed, the resin was washed 6 times with DMF. The resin was detected by ninhydrin and showed color. 16.30 g (25 mmol) of Fmoc-D-Arg(Pbf)-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin (if the resin was colorless and transparent, the reaction was terminated; if the resin was colored, the reaction was prolonged for 1 hour, the same below).

At the end of the reaction, the resin was washed 3 times with DMF. 20% piperidine/DMF (V/V) solution was added for 5+10 minutes to remove Fmoc. After the removal was completed, the resin was washed 6 times with DMF. The resin was detected by ninhydrin and showed color. 7.80 g (25 mmol) of Fmoc-D-Ala-OH, 4.05 g (30 mmol) of HOBt and 9.51 g (25 mmol) of HBTU were weighed and dissolved with 75 ml of DMF and 75 ml of DCM, and then 6.5 ml (37.5 mmol) of DIPEA was added under the condition of ice bath to activate for 5 minutes. The mixed solution was added to the reaction column and subjected to reaction at room temperature for 2 hours. The end point of the reaction was detected by ninhydrin.

The subsequent amino acids were coupled successively by the same method. After the coupling was completed, the resin was shrunk and drained to give 34.80 g of a peptide resin of fragment A: N-Ac-D-Cys(Trt)-D-Ala-D-Arg(Pbf)-D-Arg(Pbf)-D-Arg(Pbf)-D-Ala-D-Arg(Pbf)-Rink-Amide Resin.

2. Cleaving of the Crude Peptide Backbone 10 g of the obtained peptide resin was added to a round-bottom flask, shaken at room temperature for 2 hours with 102 ml of trifluoroacetic acid:$H_2O$ (95:5), and filtered. The solution after cleaving was added to anhydrous diethyl ether to give 1.40 g of a yellow solid. The yield of the crude peptide was 95.24%, and the purity of the crude peptide was 85.2%.

3. Purification of the Crude Peptide Backbone

The crude peptide backbone was purified using NOVASEP RP-HPLC system with a wavelength of 220 nm, a chromatographic column of reversed-phase C18 column, a conventional 0.1% TFA/acetonitrile as mobile phase, and desalted. Target peak fractions were collected, concentrated by rotary evaporation, and lyophilized to obtain 0.82 g of a white solid refined peptide.

4. Activation of the Sulfhydryl Group of the Cys Side Chain in the Backbone 7.7 g of 2,2'-dithiodipyridine was weighed and dissolved in 50 ml of methanol/water (3/1). 0.82 g of the backbone refined peptide was dissolved in 10 ml of water, slowly added dropwise to the 2,2'-dithiodipyridine solution, and stirred to react for 30 minutes. The reaction condition was monitored by HPLC. After the reaction was completed, the activated intermediate was purified using NOVASEP RP-HPLC system with a wavelength of 220 nm, a chromatographic column of reversed-phase C18 column, a conventional 0.1% TFA/acetonitrile as mobile phase, and desalted. Target peak fractions were collected and concentrated by rotary evaporation.

5. Modification of the Side Chain of Cys 0.242 g of H-Cys-OH was weighed, dissolved in 20 ml of water, slowly added dropwise to the activated refined peptide backbone solution, and stirred to react for 1 hour. The reaction condition was monitored by HPLC.

6. Purification of the Crude Peptide

The Etelcalcetide crude peptide obtained by the above preparation was purified using NOVASEP RP-HPLC system with a wavelength of 220 nm, a chromatographic column of reversed-phase C18 column, a conventional 0.1% TFA/acetonitrile as mobile phase, and desalted. Target peak fractions were collected, concentrated by rotary evaporation, and lyophilized to obtain 0.46 g of a white refined peptide solid with a purity detected by HPLC of 98.50% and a mass spectrometry signal of 1048.3. The total yield was 30.53%.

The above descriptions are only preferred embodiments of the present invention, and it should be noted that several improvements and modifications can further be made by one of ordinary skill in the art without departing from the principle of the present invention, which are also considered to fall within the protection scope of the present invention.

The invention claimed is:

1. A method for synthesizing Etelcalcetide, comprising the steps of:
   step 1: synthesizing by solid-phase synthesis a peptide resin of fragment A, in which protecting groups are coupled to side chains of D-Cys and D-Arg in the amino acid sequence shown in SEQ ID NO: 1, an amino resin is coupled to C-terminus of the amino acid sequence shown in SEQ ID NO: 1 and N-terminus is acetylated;
   step 2: removing the protecting group from the side chain of D-Cys in the peptide resin of fragment A to obtain a peptide resin of fragment B;
   step 3: activating sulfhydryl group of the side chain of D-Cys in the peptide resin of fragment B with 2,2'-dithiodipyridine to obtain a peptide resin of fragment C; and
   step 4: coupling L-Cys coupled with a protecting group at the N-terminus thereof to the peptide resin of fragment C in a coupling system to construct a disulfide bond, obtaining a fully protected peptide resin, and adding a cleaving solution to remove all protecting groups and amino resin to obtain a crude peptide of Etelcalcetide.

2. The method according to claim 1, wherein the step 1 is: coupling the protected D-Arg to the amino resin in the coupling system to obtain a protected D-Arg-amino resin, and according to the amino acid sequence shown in SEQ ID NO: 1 in the order from C-terminus to N-terminus, coupling protected D-Ala, protected D-Arg, protected D-Cys with N-terminal acetylation to the protected D-Argamino resin to obtain the peptide resin of fragment A.

3. The method according to claim 2, wherein the step 1 is:
   step 1.1: coupling a Fmoc-D-Arg(Pbf)-OH to the amino resin in the coupling system to obtain a Fmoc-D-Arg(Pbf)-amino resin;
   step 1.2: removing protecting group Fmoc to obtain a H-D-Arg(Pbf)-amino resin, and coupling Fmoc-D-Ala-OH to the H-D-Arg(Pbf)-amino resin in the coupling system to obtain a Fmoc-D-Ala-D-Arg(Pbf)-amino resin; and
   step 1.3: according to the amino acid sequence shown in SEQ ID NO: 1 in the order from C-terminus to N-terminus, coupling one by one sequentially three Fmoc-DArg(Pbf)-OH, Fmoc-D-Ala-OH and N-Ac-D-Cys(Mmt)-OH according to the coupling manner of step 1.2 for amino acid extension to obtain a N-Ac-D-Cys(Mmt)-D-Ala-DArg(Pbf)-D-Arg(Pbf)-D-Arg(Pbf)-D-Ala-D-Arg(Pbf)-a mino resin, that is, the peptide resin of fragment A; and
   wherein the Fmoc is a N-terminal protecting group of an amino acid, and the Pdf and Mmt are the protecting groups of an amino acid side chain.

4. The method according to claim 1, wherein the amino resin is a Rink amide resin, Rink amide AM Resin or Rink amide MBHA Resin, with a substitution degree of 0.2-1.0 mmol/g.

5. The method according to claim 1, wherein the step 2 is: removing the protecting group from the D-Cys side chain in the peptide resin of fragment A by adding a solution of TFA in DCM to the peptide resin of fragment A to obtain the peptide resin of fragment B.

6. The method according to claim 5, wherein the volume percentage of TFA in the solution of TFA in DCM is 1-3% and the balance is DCM.

7. The method according to claim 1, wherein the coupling system is HOBt/DIC coupling system with two reagents or HBTU/HOBt/DIPEA coupling system with three reagents.

8. The method according to claim 1, wherein one or both of DCM and DMF are used as a solvent in the coupling.

9. The method according to claim 1, wherein the cleaving solution is an aqueous solution of TFA.

10. The method according to claim 9, wherein the volume percentage of TFA in the cleaving solution is 95-99% and the balance is water.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial
<220> FEATURE:

```
<223> OTHER INFORMATION: All are D-amino acids

<400> SEQUENCE: 1

Cys Ala Arg Arg Arg Ala Arg
1               5
```